US012714796B2

(12) United States Patent
Coller et al.

(10) Patent No.: US 12,714,796 B2
(45) Date of Patent: Aug. 25, 2026

(54) FIXTURES FOR TESTING ELASTICITY OF DRUG DELIVERY MEMBERS AND RELATED METHODS

(71) Applicant: AMGEN INC., Thousand Oaks, CA (US)

(72) Inventors: Daniel Coller, Thousand Oaks, CA (US); Jahangir Ashraf, Thousand Oaks, CA (US); Robert W. Swift, Fillmore, CA (US); Oscar Rosas, Los Angeles, CA (US)

(73) Assignee: AMGEN INC., Thousand Oaks, CA (US)

( * ) Notice: Subject to any disclaimer, the term of this patent is extended or adjusted under 35 U.S.C. 154(b) by 951 days.

(21) Appl. No.: 17/919,673

(22) PCT Filed: Apr. 22, 2021

(86) PCT No.: PCT/US2021/028542
§ 371 (c)(1),
(2) Date: Oct. 18, 2022

(87) PCT Pub. No.: WO2021/216804
PCT Pub. Date: Oct. 28, 2021

(65) Prior Publication Data

US 2023/0148100 A1 May 11, 2023

Related U.S. Application Data

(60) Provisional application No. 63/014,006, filed on Apr. 22, 2020.

(51) Int. Cl.
*A61M 5/315* (2006.01)
*A61M 5/145* (2006.01)

(52) U.S. Cl.
CPC .... *A61M 5/31501* (2013.01); *A61M 5/14566* (2013.01)

(58) Field of Classification Search
CPC ...... A61M 5/32; A61M 3/027; A61M 3/0279; A61M 2025/0042; A61M 5/31501;
(Continued)

(56) References Cited

U.S. PATENT DOCUMENTS

| | | | | |
|---|---|---|---|---|
| 5,022,273 | A | 6/1991 | Evans | |
| 2011/0036184 | A1 | 2/2011 | Zhang | |
| 2016/0361734 | A1* | 12/2016 | Routen | B05C 5/02 |

FOREIGN PATENT DOCUMENTS

| | | | |
|---|---|---|---|
| BR | 102018016856 | A2 | 2/2020 |
| DE | 3819980 | A1 | 5/1989 |

OTHER PUBLICATIONS

Machine Translation of BR102018016856A2 (Year: 2020).*
(Continued)

*Primary Examiner* — Stephen D Meier
*Assistant Examiner* — Quang X Nguyen
(74) *Attorney, Agent, or Firm* — MARSHALL, GERSTEIN & BORUN LLP

(57) ABSTRACT

Fixtures for testing elasticity of drug related methods and related methods are disclosed. In accordance with an example, a method of testing the elasticity of a cannula of a drug delivery device includes securing a barrel of the drug delivery device within a fixture such that the cannula fixed to a distal end of the barrel extends out from the fixture. The method includes applying a lateral force to a distal end of the cannula using a strike member to move the distal end of the cannula a threshold distance. The method includes removing the force from the cannula. The method includes determining a final position of the distal end of the cannula after the force has been removed.

18 Claims, 7 Drawing Sheets

(58) Field of Classification Search
CPC ................ A61M 5/14566; G01N 3/20; G01N 2203/023; G01N 2203/0075; G01N 2203/04; G21F 5/018
See application file for complete search history.

(56) References Cited

OTHER PUBLICATIONS

International Search Report and Written Opinion issued to PCT/US2021/028542, dated Aug. 16, 2021.

Hitomi Kawamura et al., Possibility of breakage of needles for insulin self-injection and consideration of accident prevention measures, Diabetes Care, Feb. 1, 2015, vol. 12, No. 2, pp. 198-203.

Koichi Kato, Basic research on puncture resistance, injection resistance, and strength of injection needles for pen-type injectors, "BD Microfine Plus" and "Nanopass Needle", Medicine and Pharmacology, Jan. 25, 2013, vol. 69, No. 1, pp. 115-124.

Japanese Patent Application No. 2022562294, Office Action, mailed Feb. 25, 2025.

* cited by examiner

FIXTURES FOR TESTING ELASTICITY OF DRUG DELIVERY MEMBERS AND RELATED METHODS

CROSS-REFERENCE TO RELATED APPLICATION

This is the United States national phase of International Patent Application No. PCT/US2021/028542, filed Apr. 22, 2021, which claims priority to U.S. Provisional Patent Application No. 63/014,006, filed Apr. 22, 2020, the entire contents of each of which are hereby incorporated by reference herein.

FIELD OF DISCLOSURE

The present disclosure generally relates to testing drug delivery devices, and more particularly, to testing elasticity of drug delivery members, such as cannulas and/or needles.

BACKGROUND

Conventional drug delivery can be accomplished through the use of a syringe with a drug delivery member in the form of a rigid hollow cannula and/or needle, for example. For reliability and efficacy, certain standards and/or regulations may be implemented requiring that these types of cannulas/needles maintain a specific elasticity or resistance to deformation under some measure of lateral loading. It may therefore benefit manufacturers to test their cannulas/needles to ensure compliance with such standards and/or regulations.

SUMMARY

In accordance with a first example, a fixture assembly for testing the elasticity of a cannula of a drug delivery device includes a fixture block and a movable strike member. The fixture block defines a barrel receptacle and has a distal end surface. The barrel receptacle is adapted to receive the drug delivery device. The drug delivery device has a barrel and the cannula extends from a distal end of the barrel such that when the drug delivery device is received in the barrel receptacle, the cannula extends out of the fixture block and beyond the distal end surface, thereby defining the cannula as having a fulcrum point located at the distal end surface and spaced from the distal end of the barrel. The movable strike member is arranged to selectively apply a load to a distal end of the cannula spaced from the fulcrum point.

In accordance with a second example, a method of testing the elasticity of a cannula of a drug delivery device includes securing a barrel of the drug delivery device within a fixture such that the cannula fixed to a distal end of the barrel extends out from the fixture. The method includes applying a lateral force to a distal end of the cannula using a strike member to move the distal end of the cannula a threshold distance. The method includes removing the force from the cannula. The method includes determining a final position of the distal end of the cannula after the force has been removed.

In further accordance with the foregoing first and/or second examples, an apparatus and/or method may further include any one or more of the following:

In accordance with an example, the drug delivery device is disposed in the barrel receptacle.

In accordance with another example, the strike member is disposed a predetermined distance from the distal end surface and the fulcrum point of the cannula.

In accordance with another example, the predetermined distance is approximately $25*D^2$, where D is the outer diameter of the cannula in millimeters.

In accordance with another example, the fixture assembly also includes a plurality of gauge blocks for setting the predetermined distance between the strike member and the distal end surface. Each gauge block has a distinct length dimension corresponding to one of a plurality of predetermined cannula gauges.

In accordance with another example, each gauge block corresponds to a cannula gauge of between about a 10 gauge and about a 34 gauge.

In accordance with another example, the figure block includes a first fixture block and a second fixture block.

In accordance with another example, the first fixture block and the second fixture block are coupled in a clam-shell arrangement.

In accordance with another example, each fixture block has a first end, a second end, and defines a barrel groove extending between the first end and the second end and the first and second fixture blocks are adapted to be coupled together such that the barrel grooves align with each other and form the corresponding barrel receptacle.

In accordance with another example, the fixture assembly also includes a latch to secure the first fixture block and the second fixture block relative to one another.

In accordance with another example, the fixture assembly also includes a first end plate and a second end plate coupled to the second ends of the first and second fixture blocks, respectively. Each end plate defines a plunger groove. The plunger grooves collectively defines a plunger receptacle for receiving a plunger rod of the drug delivery device when the drug delivery device is disposed in the barrel receptacle.

In accordance with another example, the fixture block includes a support block that includes a top support surface and the distal end surface, and when the drug delivery device is received in the barrel receptacle, the cannula extends across the top support surface of the support block.

In accordance with another example, the fixture block is formed of a first material and the support block is formed of a second material different from the first material.

In accordance with another example, the method also includes determining an initial position of the distal end of the cannula prior to applying the force to the distal end of the cannula by moving the strike member into contact with the distal end of the cannula.

In accordance with another example, the method also includes determining a change between the final position and the initial position by moving the strike member into contact with the distal end of the cannula.

In accordance with another example, the method also includes determining a change in an angle of the cannula between the final position and the initial position.

In accordance with another example, the method includes defining a fulcrum point of the cannula a spaced distance from the distal end of the barrel.

In accordance with another example, defining the fulcrum point includes providing the fixture with a pair of fixture blocks and a support block that extends from the fixture blocks. The support block defines a top support surface supporting the cannula and a distal end surface spaced away from the distal end of the barrel of the drug delivery device and beyond which the distal end of the cannula extends, the fulcrum point of the cannula thereby being disposed at the distal end surface of the support block.

In accordance with another example, the method includes positioning the strike member a predetermined distance from the fulcrum point of the cannula prior to applying the lateral force to the distal end of the cannula.

In accordance with another example, positioning the strike member includes positioning the strike member a distance of approximately $25*D^2$, where D is the outer diameter of the cannula in millimeters, from the fulcrum point of the cannula.

In accordance with another example, positioning the strike member includes selecting a gauge block from a plurality of gauge blocks based on the outer diameter of the cannula, positioning the selected gauge block against the fixture adjacent to the cannula, and moving the strike member into contact with the selected gauge block.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

DETAILED DESCRIPTION

The present disclosure generally relates to testing fixtures used to determine the elasticity of drug delivery members, such as cannulas and/or needles (hereinafter referred to as "cannulas"). During an example elasticity test, the cannula may be bent a threshold distance for a threshold amount of time and then released. The example fixtures may be used to secure the drug delivery devices during these elasticity tests in a repeatable manner. Positioning the cannula in substantially the same location during each test allows a strike member used to move the cannula to contact substantially the same portion of the cannula. As a result, the tests can be performed substantially in the same way regardless of who or where the test is performed.

Each of the foregoing components of the drug delivery devices will now be described in more detail.

Figure 1:
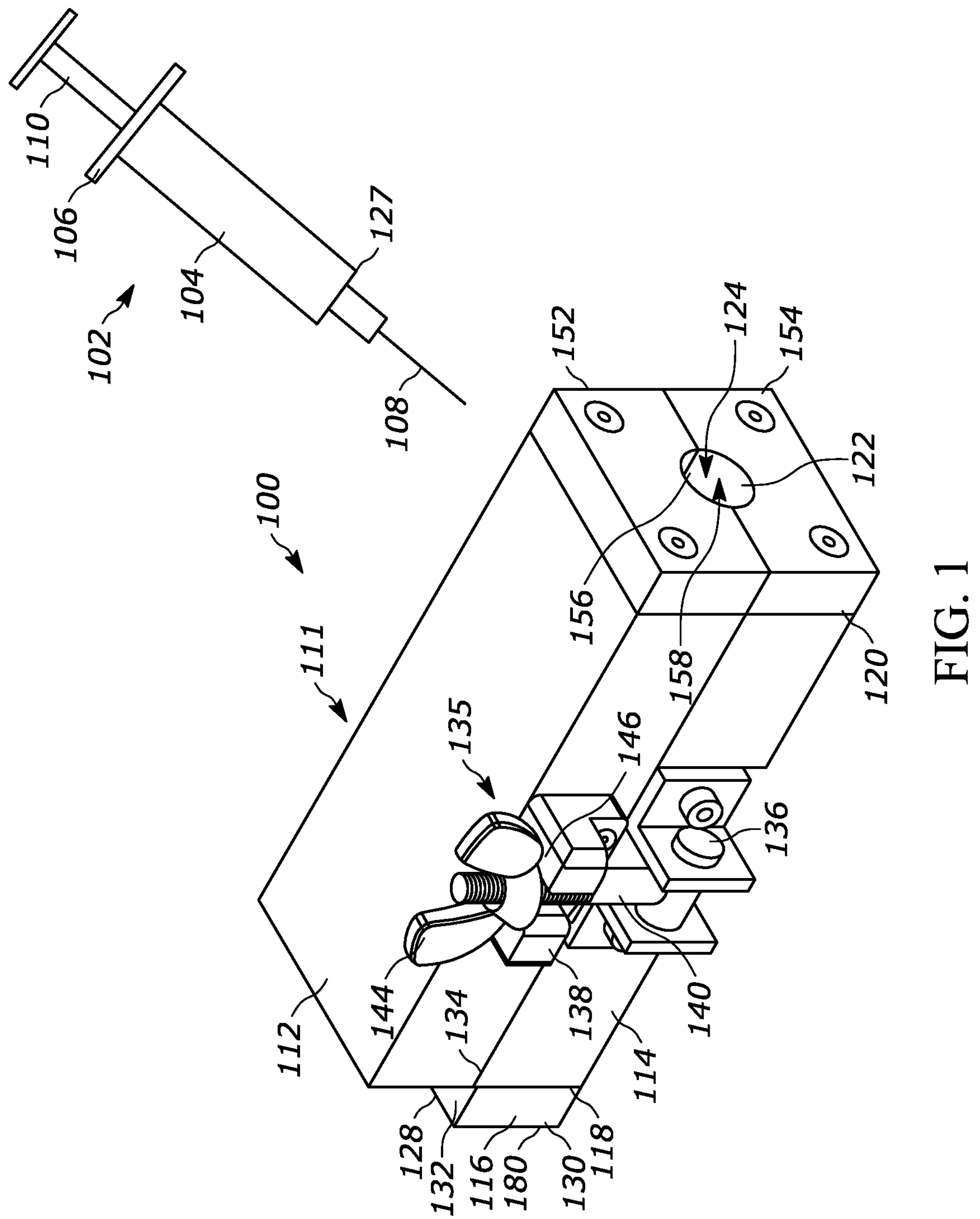
FIG. 1 is a schematic illustration of one embodiment of a fixture assembly constructed in accordance with a first example of the present disclosure.

FIG. 1 is a schematic illustration of one embodiment of a fixture assembly 100 constructed in accordance with a first example of the present disclosure. The fixture assembly 100 is used for testing a drug delivery device 102, such as the syringe shown. However, the fixture assembly 100 may alternatively be configured to test a free cannula. The drug delivery device 102 includes a barrel 104, a flange 106, and a drug delivery member such as a cannula 108 coupled with the barrel 104. The drug delivery device 102 also includes a plunger rod 110 movably disposed within the barrel 104. A plunger (not shown) may be coupled to the plunger rod 110 and slidably disposed within the barrel 104. However, the tests disclosed herein may be performed using the fixture assembly 100 with the plunger rod 110 not disposed within the barrel 104. The cannula 108 may be a rigid cannula such as a hollow needle or in some version, the cannula could be a flexible soft cannula. Generally, during an elasticity test, the drug delivery device 102 is clamped or otherwise received within and/or secured relative to the fixture assembly 100 and a force is applied to and removed from the cannula 102. Thereafter, the cannula 102 is measured to determine if the cannula 102 plastically deformed as a result of the force applied.

Referring now to the fixture assembly 100, the fixture assembly 100 includes a fixture block 111 including a first fixture block 112, a second fixture block 114, and a support 116. The first fixture block 112 may be referred to as an upper fixture block and the second fixture block 114 may be referred to as a lower fixture block. Each of the fixture blocks 112, 114 has first and second ends 118, 120 and define a barrel groove 122 (more clearly shown in FIG. 2) that extends between the ends 118, 120. The barrel grooves 122 are adapted to mate to form a barrel receptacle 124.

The support 116 is coupled to and extends from the first end 118 of the second fixture block 114. The barrel grooves 122 are adapted to receive the barrel 104 to allow the cannula 108 to lay over the support 116 and for a fulcrum point 126 (see, FIG. 5) of the cannula 108 to be spaced from a distal end 127 of the barrel 104 when the cannula 108 is bent during the elasticity test. The fulcrum point 126 may be positioned adjacent a distal end surface 128 of the support 116. The distal end surface 128 is spaced away from the first end 118 of the second fixture block 114 and forms a fulcrum for the cannula 108. In another example, the fixture block 111 may not include the first and second fixture blocks 112, 114 but may define the barrel receptacle 124 and includes the support 116. In such an example, the drug delivery device 102 may be loaded within the fixture block 111 from the second end 120 to allow the cannula 108 to extend beyond the distal end surface 128. An end cap may be included that is used to secure the drug delivery device 102 within the fixture block 111.

Because the fulcrum point 126 is spaced from the distal end 127 of the barrel 104, during the elasticity test, the cannula 108 itself is being flexed or bent. However, if the fulcrum point 126 were at the coupling between the cannula 108 and the barrel 104, the adhesive or coupling between the barrel 104 and the cannula 108 may be flexed/bent instead. Flexing the adhesive coupling may result in inaccurate test results and/or the elasticity of the cannula 108 itself not being tested.

Referring still to FIG. 1, the support 116 is a support block 130. The support block 130 has a top support surface 132 that may be substantially planer with an upper facing surface 134 of the second fixture block 114. The cannula 108 lays over the top support surface 132 when the drug delivery device 102 is secured within the fixture assembly 100.

The first fixture block 112 and the second fixture block 114 may be coupled in a clam-shell arrangement, as shown. Thus, the fixture blocks 112, 114 may be rotatably coupled.

A latch 135 is used to secure the first fixture block 112 and the second fixture block 114 relative to one another. The latch 135 may be referred to as a clamp. The latch 135 includes a male portion 136 that is rotatably coupled to the second fixture block 114 and a female portion 138 that is coupled to the first fixture block 112. The male portion 136 and the female portion 138 are shown coupled to the fixture blocks 112, 114 using fasteners (e.g., bolts). However, the male and/or female portions 136, 138 may be coupled to the fixture blocks 112, 114 in different ways. For example, the male and/or female portions 136, 138 may be brazed to the corresponding fixture blocks 112, 114 and/or adhesive may be used.

In the example shown, the male portion 136 includes an elongated fastener 140 having a threaded end that extends through a slot 142 of the female portion 138. A nut 144 is threaded onto the male portion 136 and is driven against a face 146 of the female portion 138 to secure the fixture blocks 112, 114 together. However, in another example, the fixture blocks 112, 114 may be coupled in a different way. For example, a plurality of fasteners may be used to couple the first fixture block 112 and the second fixture block 114 together. Other methods may prove suitable.

An upper end plate 152 and a lower end plate 154 may be included that are coupled to the second end 120 of the corresponding fixture block 112, 114. The end plates 152, 154 are shown being coupled to the fixture blocks 112, 114 using fasteners. Other methods of coupling the end plates 152, 154 and the fixture blocks 112, 114 may prove suitable. In the example shown, each of the end plates 152, 154 define a plunger groove 156 that mate with one another and form a plunger receptacle 158. When the drug delivery device 102 is secured in the fixture assembly 100, the plunger rod 110 of the drug delivery device 102 may extend through the plunger receptacle 158.

The fixture blocks 112, 114 may be formed of a first material and the support 116 may be formed of a second material. In an example, the fixture blocks 112, 114 are formed of metal such as Aluminum and the support 116 is formed of plastic such as polyether ether ketone PEEK. Using PEEK for the support 116 may reduce abrasion of the cannula 108. However, other materials may prove suitable to form the fixture blocks 112, 114, and/or the support 116 and the fixture blocks 112, 114, and/or the support 116 may be formed of the same or different materials.

Figure 2:
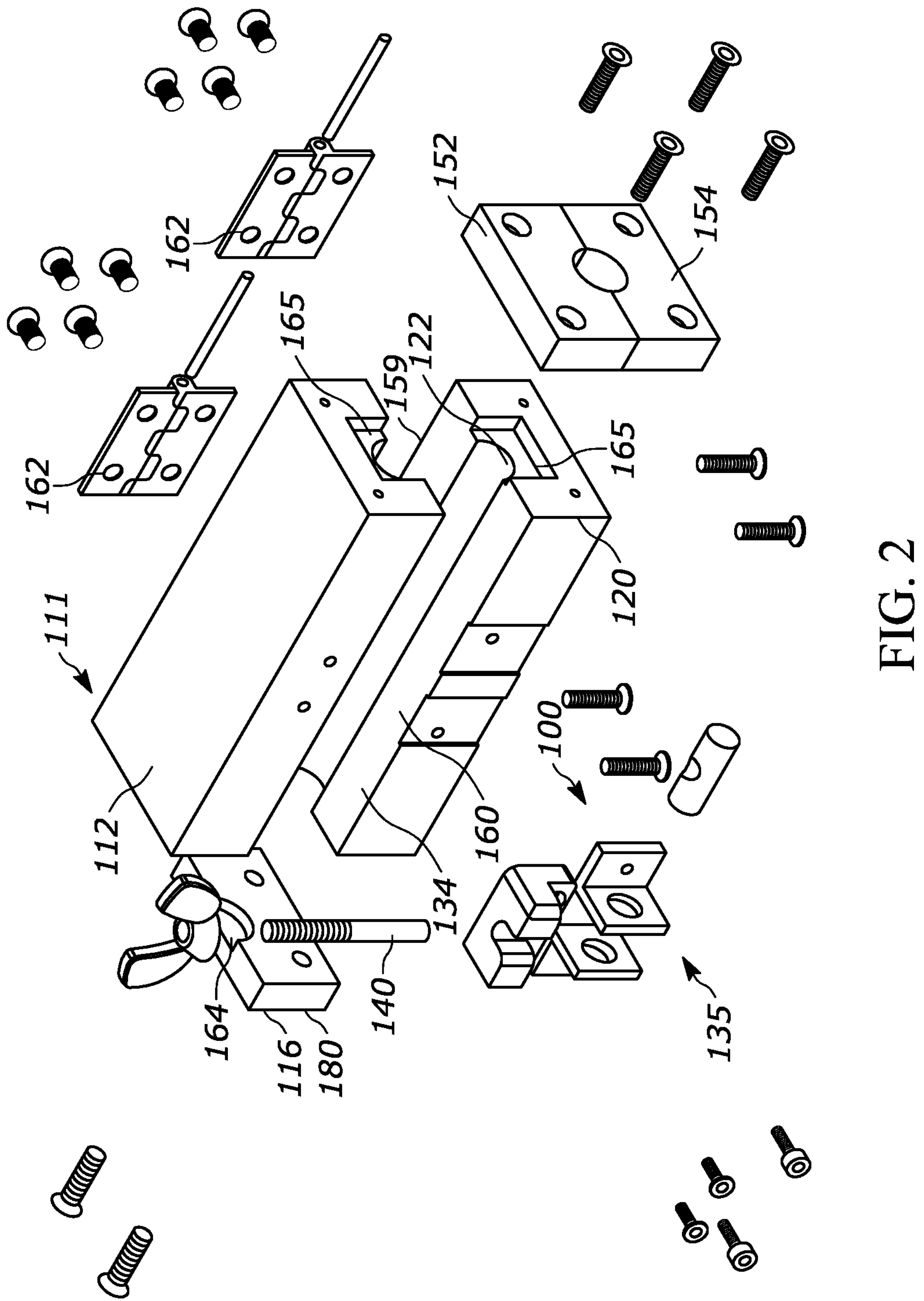
FIG. 2 is an expanded view of the fixture assembly of FIG. 1.

FIG. 2 is an expanded view of the fixture assembly 100 of FIG. 1. The fixture blocks 112, 114 include lateral sides 159, 160 and, in the example shown, are rotatably coupled at the lateral side 159 by a hinge 162. While two hinges 162 are shown, any number of hinges may be included instead. The latch 135 is used to selectively couple the fixture blocks 112, 114 at the second lateral side 160.

In the example shown, the support 116 includes a barrel seat 164 that is adapted to receive an end of the barrel 104 of the drug delivery device 102. During the elasticity test, the distal end 127 of the barrel 104 may bear against the barrel seat 164. The barrel seat 164 may be referred to as a cut out. The barrel seat 164 may be formed by a semi-circular groove or may otherwise have a cross-section that corresponds to at least a portion of the cross-section of the drug delivery device 102. In other implementations and based on the length of the drug delivery device 102 being tested (e.g., the length of the barrel 104), the barrel seat 164 may be modified in shape, dimension, etc., and/or may be omitted. Moreover, additional or alternative changes to the fixture assembly 100 may occur to accommodate different styles and/or brands of drug delivery devices produced by the same or different manufactures. For example, in some implementations, centering pieces (e.g., strips, o-rings, or other constructs) may be used in conjunction with the fixture blocks 112, 114 to account for syringe barrels, for example, having different physical shapes and/or dimensions. In one contemplated version, for example, the fixture blocks 112, 114 may define opposing grooves that are connected to and outwardly extending from the corresponding barrel grooves 122, transvers to the longitudinal dimension of the barrel grooves 122. These opposing grooves may receive an elastomer material in the form of a rubber strip, for example, that is used to center and/or secure the drug delivery device 102, the barrel 104, and/or the cannula 108 relative to the fixture assembly 100. Other configurations are possible.

The fixture blocks 112, 114 also each define a flange groove 165 adjacent the second end 120. The flange grooves 165 are adapted to mate and receive the flange 106 of the drug delivery device 102. The flange grooves 165 enable the drug delivery device 102 to be positioned in substantially the same fixed location during the elasticity tests performed on the different drug delivery devices. The end plates 152, 154 also form a portion of the flange grooves 165 when they are coupled to the fixture blocks 112, 114.

FIGS. 3-6 depict a process of using the fixture assembly 100 during an elasticity test.

Figure 3:
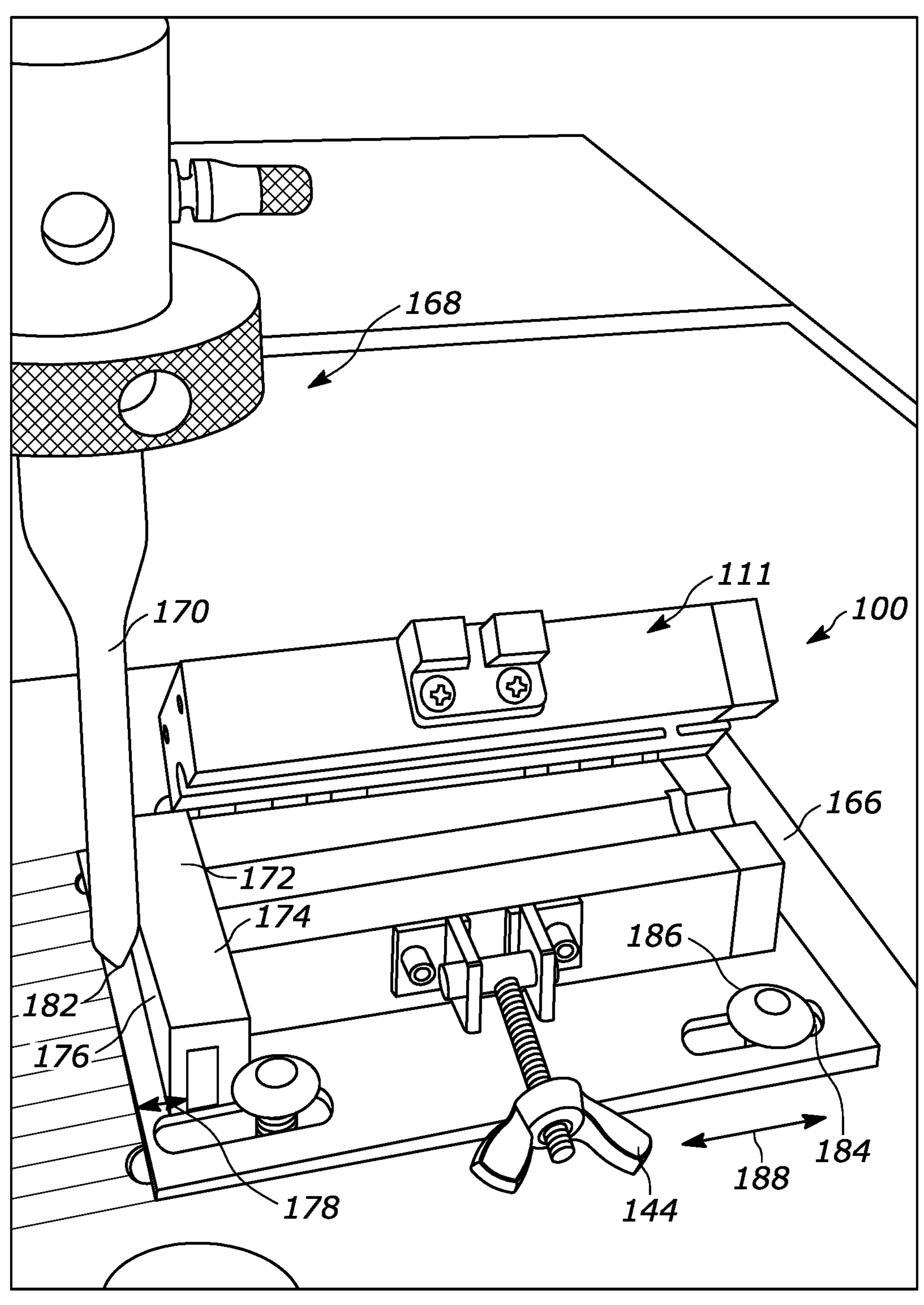
FIG. 3 is an isometric view of the fixture assembly of FIG. 1 secured to a base plate of a compression testing machine including a strike member.

FIG. 3 is an isometric view of the fixture assembly 100 of FIG. 1 secured to a base plate 166 of a compression testing machine 168. The compression testing machine 168 includes a strike member 170 shown as a strike pin. The compression testing machine 168 may be a force testing machine.

In the example shown, a gauge 172 is positioned on the support 116. The gauge 172 may be referred to as a gauge block. The gauge 172 is L-shaped and includes an upper leg 174 and a lower leg 176.

In practice, the gauge 172 is used to define a distance 178 between a face 180 (see, FIG. 1) of the support 116 and the strike member 170. In some examples, the distance 178 is defined by Equation 1, where D corresponds to the distance 178 and the diameter corresponds to an outer diameter of the cannula 108. The diameter of the cannula 108 may be in millimeters and the distance 178 may be in millimeters. It is noted that the distance, D, is a length measurement even though the $\text{Diameter}^2$ is an area measurement. In an example, the outer diameter of the cannula 108 is about 1.0 millimeter.

$$D = 25(\text{Diameter}^2) \qquad \text{Equation 1}$$

An end 182 of the strike member 170 is adapted to engage and move a distal end 171 of the cannula 108 during the elasticity test, for example. The distal end 171 of the cannula 108 extends from the fixture assembly 100. The strike member 170 may be pointed or rounded.

To position the strike member 170 to engage the gauge 172 and define the distance 178, the fixture assembly 100 and the gauge 172 may be moved toward the strike member 170. After the gauge 172 engages the strike member 170 and the gauge 172 and the fixture assembly 100 are unable to be further moved toward the strike member 170, the fixture assembly 100 is secured to the base plate 166. In the example shown, the fixture assembly 100 includes slots 184 through which fasteners 186 extend and couple the fixture assembly 100 to the compression testing machine 168. An interaction between the fasteners 186 and the slots 184 allows the fixture assembly 100 to move in a direction generally indicated by arrow 188.

While the gauge 172 is shown in FIG. 3, different gauge blocks may be used. For example, a plurality of gauge blocks may be provided where each of the gauge blocks has a distinct length dimension (e.g., a width) associated with a different cannula gauge (e.g., needle gauge). The gauge blocks including the gauge 172 may be used with a cannula gauge of between about a 10 gauge and about a 34 gauge. In an example, the gauge 172 is associated with a cannula having a 20 gauge, a 21 gauge, a 22 gauge, a 23 gauge, a 25 gauge, a 29 gauge, a 30 gauge, or a 31 gauge.

Prior to determining the elasticity of the cannula 108, the strike member 170 may also be zeroed by touching the strike member 170 to the fixture assembly 100 and/or the support 116 until a force of between about 1 Newton (N) and about 5 N is recorded. The axial height may be defined as "zero." When and/or before the elasticity test begins, the strike member 170 may be moved above the fixture assembly 100 to allow the drug delivery device 102 to be secured within the fixture assembly 100.

Figure 4:
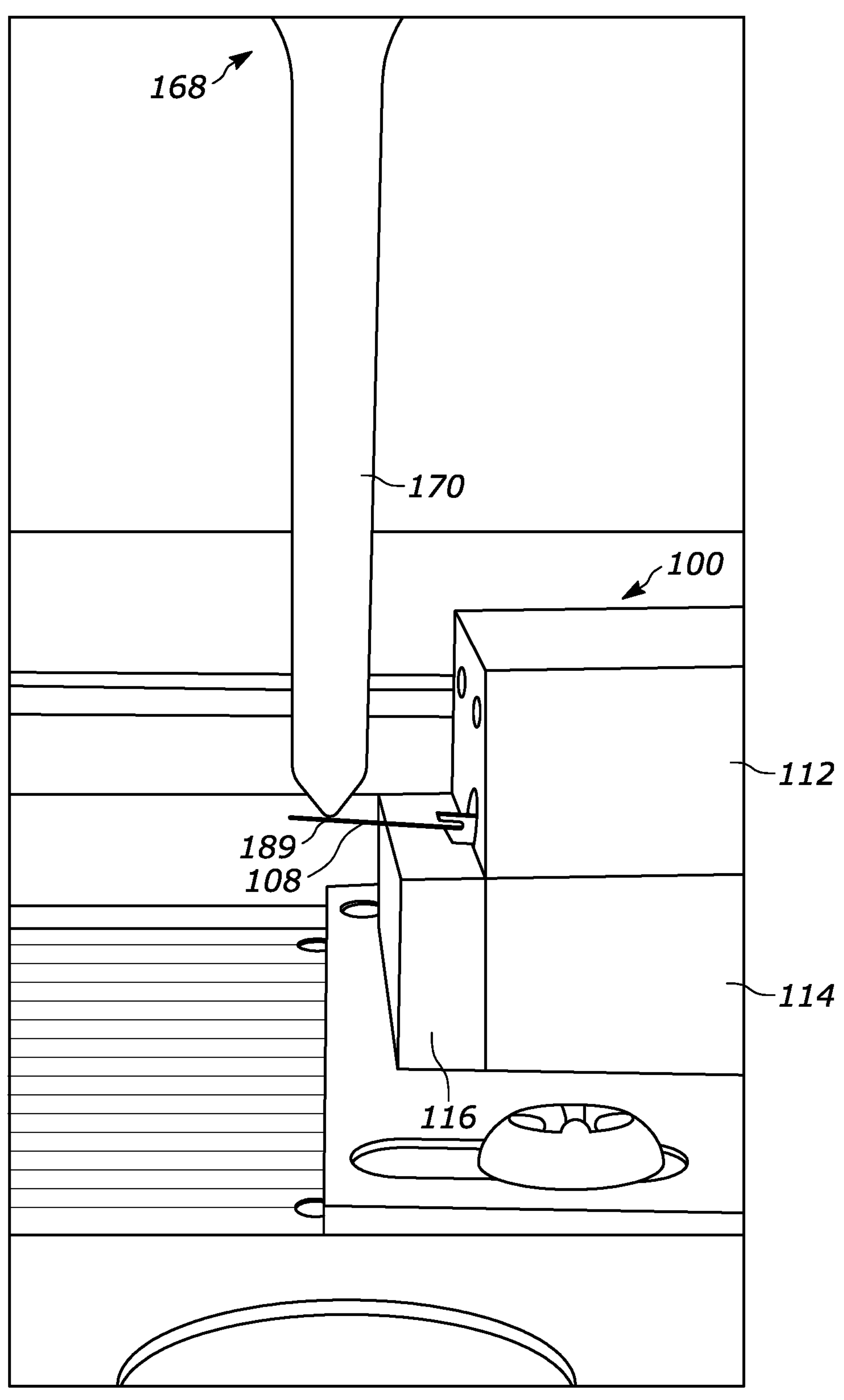
FIG. 4 is an isometric side view of a portion of the fixture assembly securing the barrel of the drug delivery device and the strike member engaging the cannula to allow an initial position of the cannula to be determined.

FIG. 4 is an isometric side view of a portion of the fixture assembly 100 securing the barrel 104 of the drug delivery device 102 and the strike member 170 engaging the cannula 108 to allow an initial position of the cannula 108 to be determined. With the drug delivery device 102 secured within the fixture assembly 100, the cannula 108 staked to the barrel 104 is allowed to extend from the fixture assembly 100. The cannula 108 is shown overlaying the support 116 and extending beyond the distal end surface 128 of the support block 116. In the example shown, the strike member 170 is shown touching the cannula 108 to allow the compression testing machine 168 to determine an initial position of the cannula 108 prior to the strike member 170 bending/moving the cannula 108 during the elasticity test.

In an example, when the strike member 170 initially contacts the cannula 108, the strike member 170 approaches the cannula 108 at a speed of about 5 millimeters (mm)/minute. However, the strike member 170 may approach the cannula 108 at a speed of about 0.1 mm/min to about 500 mm/min or another speed. The strike member 170 may contact the cannula 108 at a portion 189 on the cannula 108 that is defined by the distance 178 set by the gauge 172. The strike member 170 may stop moving for approximately one second after a force of about 0.15 N is recorded. The axial distance of the strike member 170 may be recorded as the initial position of the cannula 108 and represented by $P_i$.

Figure 5:
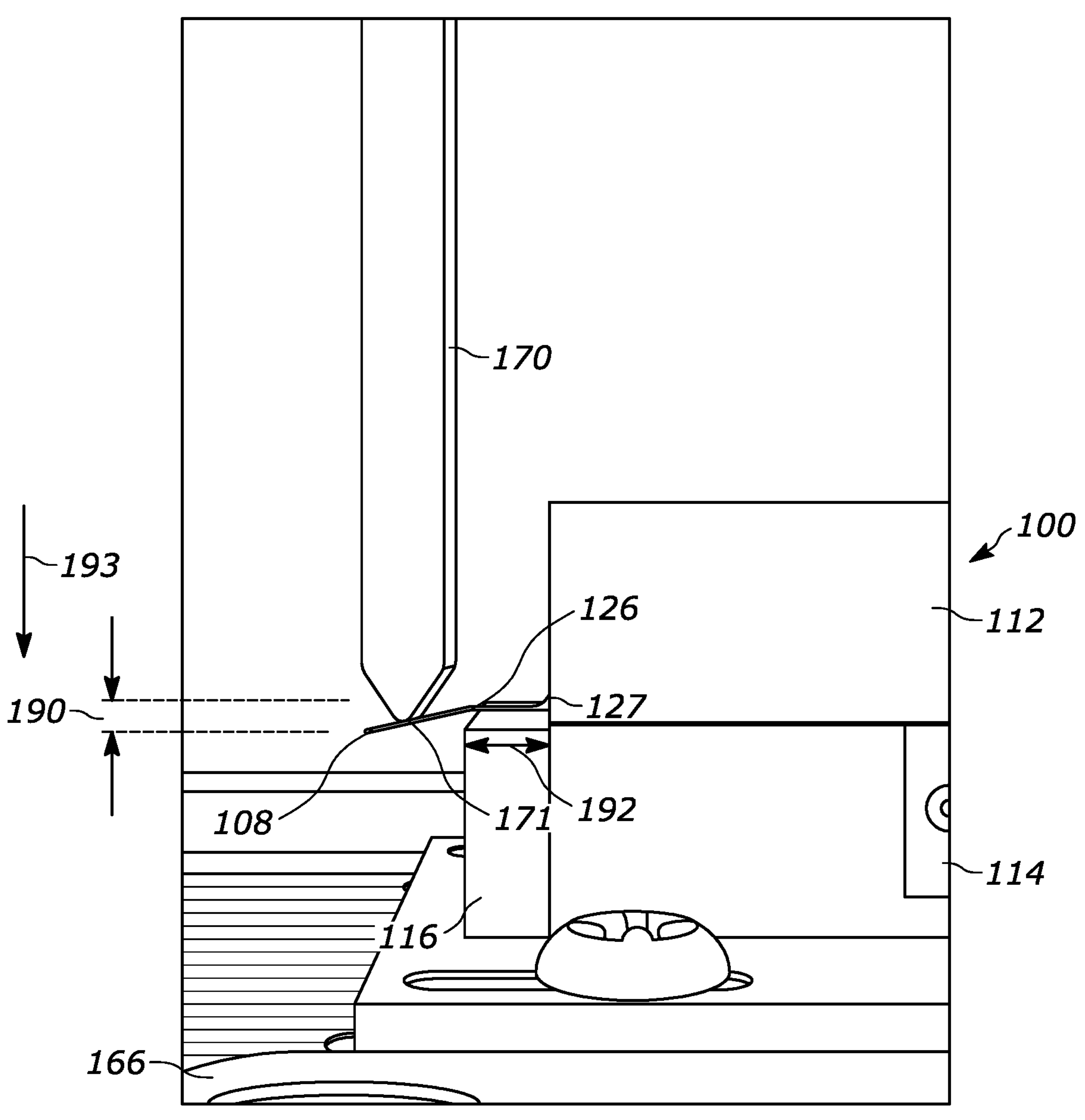
FIG. 5 is an isometric side view of the portion of the fixture assembly shown in FIG. 4 with the strike member applying a force to the cannula to move the cannula a threshold distance.

FIG. 5 is an isometric side view of the portion of the fixture assembly 100 shown in FIG. 4 with the strike member 170 applying a force to the cannula 108 to move the cannula 108 a threshold distance 190. The threshold distance 190 may be referred to as a test condition or a threshold amount. During the elasticity test, the strike member 170 may bend the cannula 108 a given bend angle in degrees, a given axial distance, and/or with a particular amount of force for a threshold amount of time. The fulcrum point 126 is shown being spaced a distance 192 from the distal end 127 of the barrel 104 of the drug delivery device 102 and being formed over the support 116.

In an example, during the elasticity test, the strike member 170 applies a lateral force to the cannula 108 in the direction indicated by arrow 193 and toward the base plate 166 at a speed of approximately 5 mm/min. In another example, the strike member 170 may be moved toward the base plate 166 at a speed of about 0.1 mm/min to about 500 mm/min until the threshold distance is met. As an example, some elasticity tests require that the cannula 108 be bent to an angle of 12 degrees from the initial position and held at 12 degrees for 60 seconds. However, the elasticity tests of different countries may have different requirements.

Figure 6:
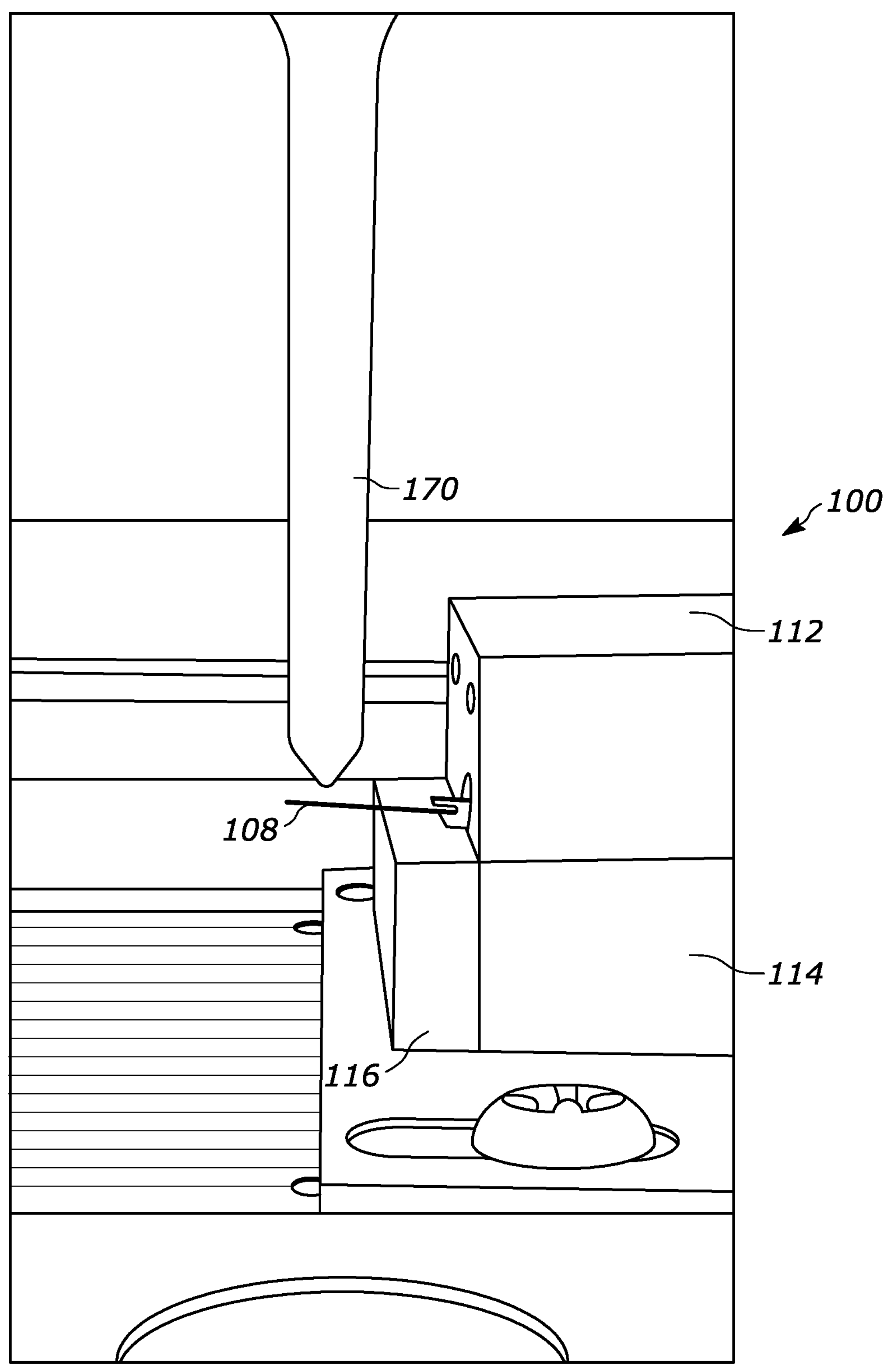
FIG. 6 is an isometric view of the portion of the fixture assembly shown in FIG. 4 with the force from the strike member removed.

FIG. 6 is an isometric view of the portion of the fixture assembly 100 shown in FIG. 4 with the force from the strike member 170 removed. Thus, the cannula 108 has been allowed to move to its natural state and/or to its final position after being moved by the strike member 170. In an example, after the threshold distance 190 is satisfied, the strike member 170 may be moved away from the cannula 108 at a speed of approximately 500 mm/min. In another example, the strike member 170 may be moved away from the cannula 108 at any speed of between about 0.1 mm/min to about 2000 mm/min. Other speeds of moving the strike member 170 may prove suitable.

Figure 7:
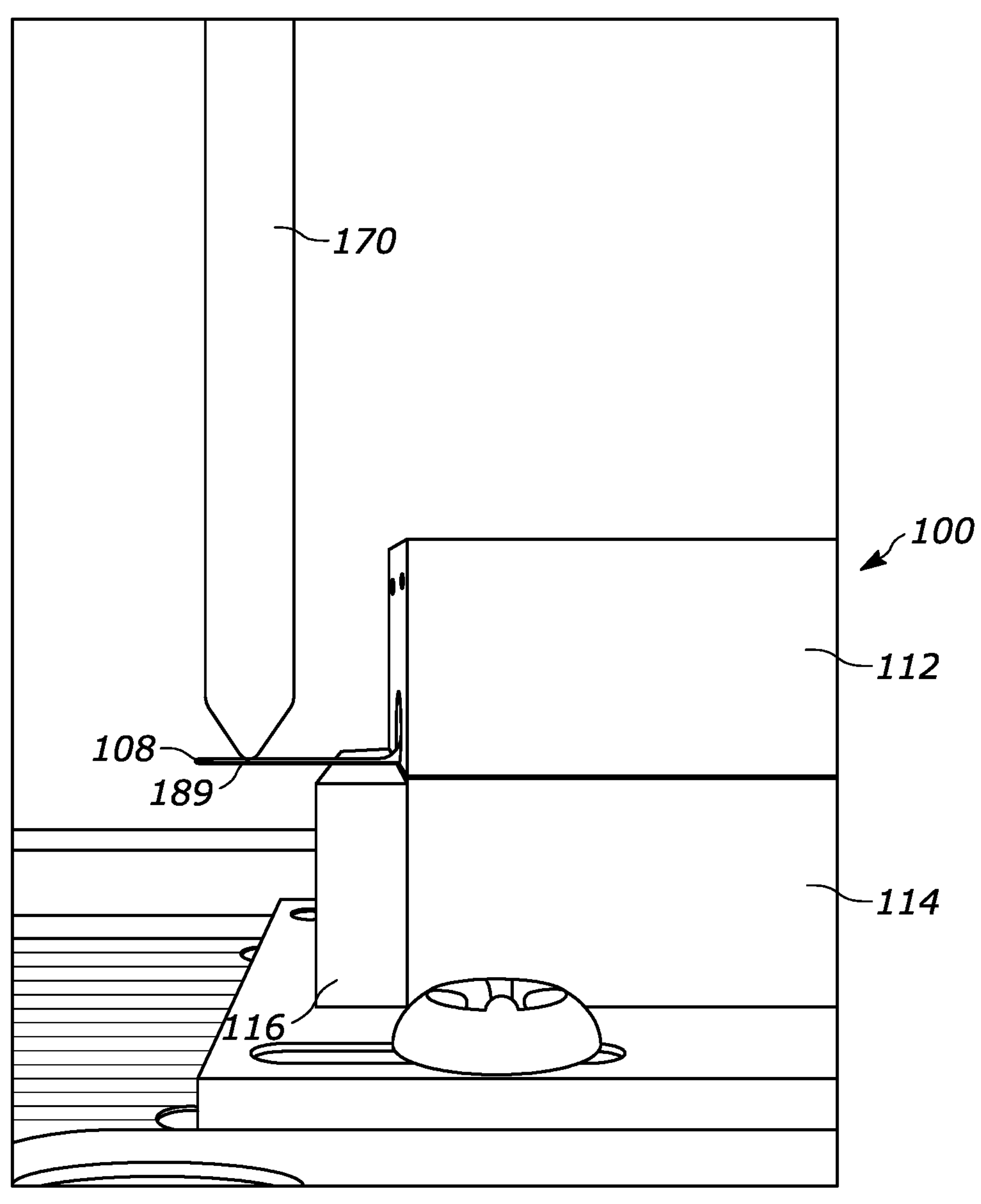
FIG. 7 is an isometric view of the portion of the fixture assembly shown in FIG. 4 with the strike member determining a final position of the cannula after the force has been removed.

FIG. 7 is an isometric view of the portion of the fixture assembly 100 shown in FIG. 4 with the strike member 170 determining a final position of the cannula 108 after the force has been removed. The cannula 108 may be inspected to determine if the cannula 108 has returned to its initial position or if plastic deformation has occurred while the cannula 108 was under load. Thus, using the disclosed examples, plastic deformation (if any) of the cannula 108 can be quantified by measuring a change between an initial position of the cannula 108 and a final position of the cannula 108. The change between the initial and final positions may be defined in millimeters or a deflection angle in degrees.

An output on the results of the elasticity test may be generated by the compressible testing machine 108. The results may be displayed using different methods such as displaying the results on a user interface, providing access to the results at a different device, printing the results, etc.

In an example, to determine the final position of the cannula 108, the strike member 170 may approach the cannula 108 at a speed of about 5 mm/min. In another example, the strike member 170 may move toward the cannula 108 at a speed of between about 0.1 mm/min to about 500 mm/min. The strike member 170 may contact the cannula 108 at the portion 189 of the cannula 108 and stop moving for approximately 1 second after a force of approximately 0.15 N is recorded. The axial distance of the strike member 170 may be recorded as the final position of the cannula 108 and represented by $P_f$.

Equation 2 may be used to determine the change in the position (bend) of the cannula 108, where $P_i$ is the initial position of the cannula 108 in millimeters, $P_f$, is the final position of the cannula 108 in millimeters, D is the nominal outer diameter of the cannula 108 in millimeters, and the deflection angle is the angle formed by the initial position and the final position of the cannula 108 after having the force applied at the portion 189 of the cannula 108.

$$\text{Deflection Angle} = \tan^{-1}\left[\frac{P_f - P_i}{25D^2}\right] \quad \text{Equation: 2}$$

The deflection may also be reported as the distance, $P_f - P_i$

While the present disclosure has been described in connection with various embodiments, it will be understood that the present disclosure is capable of further modifications. The present disclosure is intended to cover any variations, uses, or adaptations of the disclosed subject matter following, in general, the principles of the present disclosure, and including such departures from the present disclosure as, within the known and customary practice within the art to which the present disclosure pertains.

It is noted that the construction and arrangement of the drug delivery device and its various components and assemblies as shown in the various exemplary embodiments is illustrative only. Although only a few embodiments of the subject matter at issue have been described in detail in the present disclosure, those skilled in the art who review the present disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed herein. For example, elements shown as integrally formed may be constructed of multiple parts or elements, and vice versa. Also, the position of elements may be reversed or otherwise varied, and the nature or number of discrete elements or positions may be altered or varied. Accordingly, all such modifications are intended to be included within the scope of the present disclosure as defined in the appended claims. Furthermore, the order or sequence of any process or method steps may be varied or re-sequenced according to alternative embodiments. Other substitutions, modifications, changes and omissions may be made in the design, operating conditions and arrangement of the various exemplary embodiments without departing from the scope of the present disclosure.

What is claimed is:

1. A fixture assembly for testing the elasticity of a cannula of a drug delivery device, the fixture assembly comprising:

a fixture block defining a barrel receptacle and having a distal end surface, wherein the barrel receptacle is adapted to receive the drug delivery device, the drug delivery device having a barrel and the cannula extending from a distal end of the barrel such that when the drug delivery device is received in the barrel receptacle, the cannula extends out of the fixture block and beyond the distal end surface, thereby defining the cannula as having a fulcrum point located at the distal end surface and spaced from the distal end of the barrel; and a movable strike member arranged to selectively apply a load to a distal end of the cannula spaced from the fulcrum point, wherein the fixture block comprises a support block comprising a top support surface and the distal end surface, and wherein when the drug delivery device is received in the barrel receptacle, the cannula extends across the top support surface of the support block.

2. The fixture assembly of claim 1, further comprising the drug delivery device disposed in the barrel receptacle.

3. The fixture assembly of claim 1, wherein the strike member is disposed a predetermined distance from the distal end surface and the fulcrum point of the cannula.

4. The fixture assembly of claim 3, wherein the predetermined distance is approximately $25*D^2$, where D is the outer diameter of the cannula in millimeters.

5. The fixture assembly of claim 1, wherein the fixture block includes a first fixture block and a second fixture block.

6. The fixture assembly of claim 5, wherein the first fixture block and the second fixture block are coupled in a clam-shell arrangement.

7. The fixture assembly of claim 5, wherein each fixture block has a first end, a second end, and defines a barrel groove extending between the first end and the second end and wherein the first and second fixture blocks are adapted to be coupled together such that the barrel grooves align with each other and form the corresponding barrel receptacle.

8. The fixture assembly of claim 5, further comprising a latch to secure the first fixture block and the second fixture block relative to one another.

9. The fixture assembly of claim 5, further comprising a first end plate and a second end plate coupled to the second ends of the first and second fixture blocks, respectively, each end plate defining a plunger groove, the plunger grooves collectively defining a plunger receptacle for receiving a plunger rod of the drug delivery device when the drug delivery device is disposed in the barrel receptacle.

10. A fixture assembly for testing the elasticity of a cannula of a drug delivery device, the fixture assembly comprising:

a fixture block defining a barrel receptacle and having a distal end surface, wherein the barrel receptacle is adapted to receive the drug delivery device, the drug delivery device having a barrel and the cannula extending from a distal end of the barrel such that when the drug delivery device is received in the barrel receptacle, the cannula extends out of the fixture block and beyond the distal end surface, thereby defining the cannula as having a fulcrum point located at the distal end surface and spaced from the distal end of the barrel; and a movable strike member arranged to selectively apply a load to a distal end of the cannula spaced from the fulcrum point, wherein the strike member is disposed a predetermined distance from the distal end surface and the fulcrum point of the cannula, and further comprising a plurality of gauge blocks for setting the predetermined distance between the strike member and the distal end surface, each gauge block having a distinct length dimension corresponding to one of a plurality of predetermined cannula gauges.

11. The fixture assembly of claim 10, wherein each gauge block corresponds to a cannula gauge of between about a 10 gauge and about a 34 gauge.

12. A method of testing the elasticity of a cannula of a drug delivery device comprising:

securing a barrel of the drug delivery device within a fixture such that the cannula fixed to a distal end of the barrel extends out from the fixture;

applying a lateral force to a distal end of the cannula using a strike member to move the distal end of the cannula a threshold distance;

removing the force from the cannula; and determining a final position of the distal end of the cannula after the force has been removed, and defining a fulcrum point of the cannula a spaced distance from the distal end of the barrel, wherein defining the fulcrum point comprises providing the fixture with a pair of fixture blocks and a support block that extends from the fixture blocks, the support block defining a top support surface supporting the cannula and a distal end surface spaced away from the distal end of the barrel of the drug delivery device and beyond which the distal end of the cannula extends, the fulcrum point of the cannula thereby being disposed at the distal end surface of the support block.

13. The method of claim 12, further comprising determining an initial position of the distal end of the cannula prior to applying the force to the distal end of the cannula by moving the strike member into contact with the distal end of the cannula.

14. The method of claim 13, further comprising determining a change between the final position and the initial position by moving the strike member into contact with the distal end of the cannula.

15. The method of claim 12, further comprising (a) determining a change in an angle of the cannula between the final position and the initial position, and/or (b) defining a fulcrum point of the cannula a spaced distance from the distal end of the barrel.

16. The method of claim 12, further comprising positioning the strike member a predetermined distance from the fulcrum point of the cannula prior to applying the lateral force to the distal end of the cannula.

17. The method of claim 16, wherein positioning the strike member comprises positioning the strike member a distance of approximately $25*D^2$, where D is the outer diameter of the cannula in millimeters, from the fulcrum point of the cannula.

18. The method of claim 16, wherein positioning the strike member comprises selecting a gauge block from a plurality of gauge blocks based on the outer diameter of the cannula, positioning the selected gauge block against the fixture adjacent to the cannula, and moving the strike member into contact with the selected gauge block.

* * * * *